United States Patent
Gunasekaran et al.

(10) Patent No.: US 10,794,833 B2
(45) Date of Patent: Oct. 6, 2020

(54) PACKAGING AND METHODS FOR DETECTING EXPOSURE OF A PERISHABLE GOOD TO AN ELEVATED TEMPERATURE

(71) Applicant: Wisconsin Alumni Research Foundation, Madison, WI (US)

(72) Inventors: Sundaram Gunasekaran, Madison, WI (US); Seok won Lim, Seoul (KR)

(73) Assignee: WISCONSIN ALUMNI RESEARCH FOUNDATION, Madison, WI (US)

(*) Notice: Subject to any disclaimer, the term of this patent is extended or adjusted under 35 U.S.C. 154(b) by 348 days.

(21) Appl. No.: 15/844,256

(22) Filed: Dec. 15, 2017

(65) Prior Publication Data

US 2018/0172598 A1    Jun. 21, 2018

Related U.S. Application Data

(63) Continuation of application No. 13/209,947, filed on Aug. 15, 2011, now abandoned.

(60) Provisional application No. 61/374,127, filed on Aug. 16, 2010.

(51) Int. Cl.
| | | |
|---|---|---|
| *G01N 21/78* | (2006.01) | |
| *G01N 21/27* | (2006.01) | |
| *G01N 33/20* | (2019.01) | |
| *G01N 33/02* | (2006.01) | |
| *G01K 3/04* | (2006.01) | |
| *G01K 11/12* | (2006.01) | |

(52) U.S. Cl.
CPC ............. *G01N 21/78* (2013.01); *G01K 3/04* (2013.01); *G01N 21/272* (2013.01); *G01N 33/20* (2013.01); *G01K 11/12* (2013.01); *G01N 33/02* (2013.01)

(58) Field of Classification Search
CPC ........ G01K 11/12; G01K 3/04; G01N 21/272; G01N 21/78; G01N 33/20; G01N 33/02
USPC ........ 436/20, 73, 80, 86, 164, 165; 422/400, 422/401, 402, 82.05, 82.09, 547
See application file for complete search history.

(56) References Cited

U.S. PATENT DOCUMENTS

| | | | |
|---|---|---|---|
| 4,737,463 A * | 4/1988 | Bhattacharjee | G01N 31/229 116/206 |
| 5,085,802 A | 2/1992 | Jalinski | |
| 6,103,351 A * | 8/2000 | Ram | G01K 3/04 116/219 |
| 6,544,925 B1 | 4/2003 | Prusik et al. | |
| 7,430,982 B2 * | 10/2008 | Koivukunnas | G01K 3/04 116/207 |

(Continued)

OTHER PUBLICATIONS

Brayner, R. et al., "Preparation and characterization of metal (Au)—and bimetallic alloys (AuNi)—gelatin nanocomposites," (2005) *Colloids and Surfaces A: Physicochem. Eng. Aspects* 256:191-197.

(Continued)

*Primary Examiner* — Maureen Wallenhorst
(74) *Attorney, Agent, or Firm* — Quarles & Brady LLP

(57) ABSTRACT

Nanoreactors having a metal precursor in a carrier are provided. In some embodiments, upon exposure to heat, the metal precursor forms nanoparticles that can be detected, e.g., by detecting a color change in the nanoreactor and/or by detecting the number and/or size and/or size distribution and/or shape of the nanoparticles. The nanoreactors can be used, in some embodiments, as time-temperature indicators for perishable goods.

21 Claims, 8 Drawing Sheets

(56) References Cited

U.S. PATENT DOCUMENTS

| | | | | |
|---|---|---|---|---|
| 2010/0209521 A1* | 8/2010 | Schalkhammer | ...... | G01N 21/78 424/497 |
| 2010/0273665 A1* | 10/2010 | Haick | ...... | B82Y 15/00 506/8 |

OTHER PUBLICATIONS

Daniel, M.-C. et al., "Gold nanoparticles: Assembly, supramolecular chemistry, quantum-size-related properties, and applications toward biology, catalysis, and nanotechnology," (2004) *Chem. Rev.* 104:293-346.

Finney, E, et al., "Nanocluster nucleation and growth kinetic and mechanistic studies: A review emphasizing transition-metal nanoclusters," (2007) *Journal of Colloid and Interface Science* 317:351-374.

Frokjaer, S. et al., "Protein drug stability: A formulation challenge," (2005) *Nature Review Drug Discovery* 4:298-306.

Ghosh, S. K. et al., "Interparticle coupling effect on the surface plasmon resonance of gold nanoparticles: From theory to applications," (2007) *Chem. Rev.* 107:4797-4862.

Gunasekaran et al., "A nanomaterial-based food thermal history indicator," (2011) Abstract, IFT Annual Meeting.

Lim et al., "Gelatin-Templated Gold Nanoparticles as Novel Time-Temperature Indicator," (2012) J. Food Sci 77:9 N45-N49.

Neupane et al., "Synthesis of gelatin-capped gold nanoparticles with variable gelatin concentration," (2010) J Nanopart Res. 13 491-498.

Pal, T., "Gelatin—A compound for all reasons," (1994) *Journal of Chemical Education* 71:679-681.

Patakfalvi, R, et al., "The kinetics of homogeneous nucleation of silver nanoparticles stabilized by polymers," (2007) *Journal of Nanoparticle Research* 9:353-364.

Ray, P.C. Size and shape dependent second order nonlinear optical properties of nanomaterials and their application in biological and chemical sensing. Chem Rev 2010, 110:5332-5365.

Sardar, R. & Shumaker-Parry, J.S. Spectroscopic and microscopic investigation of gold nanoparticle formation: ligand and temperature effects on rate and particle size. J Am Chem Soc 2011, 133:8179-8190.

Sugimoto, T., "Formation of Monodispersed Nano- and Micro-Particles Controlled in Size, Shape, and Internal Structure," (2003) *Cheml Eng Technol* 26:313-321.

Wang, Y-C & Gunasekaran, S. Spectroscopic and microscopic investigation of gold nanoparticle nucleation and growth mechanisms using gelatin as a stabilizer. J Nanopart Res 2012, 14:1-11.

Yu, Y. et al., "Gold nanorods: Electrochemical synthesis and optical properties," (1997) *Journal of Physical Chemistry* 101:6661-6664.

Zhang et al., "Synthesis of Gelatin-Stabilized Gold Nanoparticles and Assembly of Carboxylic Single-Walled Carbon Nanotubes/Au Composites for Cytosensing and Drug Uptake," (2009) *Anal. Chem.* 81:16 6641-6648.

Zeisberg, M. et al., "Biomarkers for epithelial-mesenchymal transitions," (2009) *Journal of Clinical Investigation* 119(6):1429-1437.

U.S. Appl. No. 13/209,947, filed Aug. 15, 2011.

Office Action dated Oct. 21, 2014 in U.S. Appl. No. 13/209,947.

Office Action dated May 4, 2015 in U.S. Appl. No. 13/209,947.

Office Action dated Dec. 30, 2015 in U.S. Appl. No. 13/209,947.

Office Action dated Sep. 7, 2016 in U.S. Appl. No. 13/209,947.

Office action dated Mar. 22, 2017 in U.S. Appl. No. 13/209,947.

Office action dated Sep. 15, 2017 in U.S. Appl. No. 13/209,947.

* cited by examiner

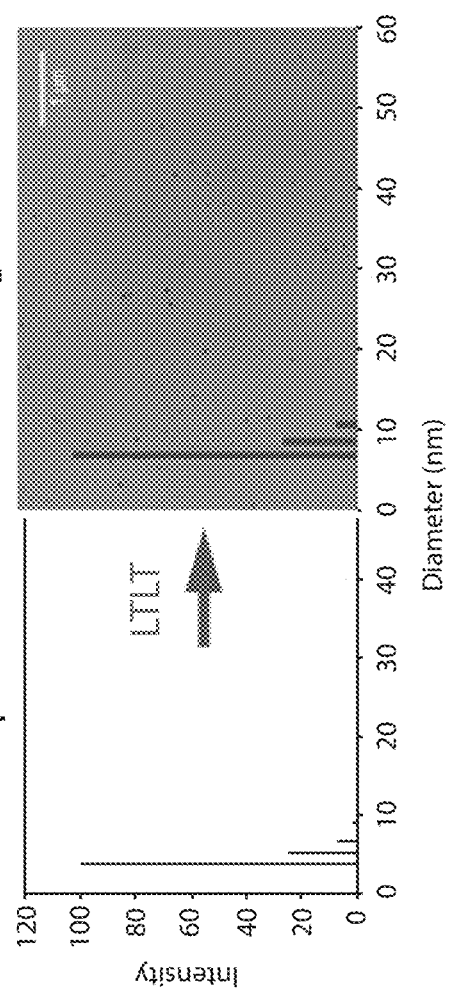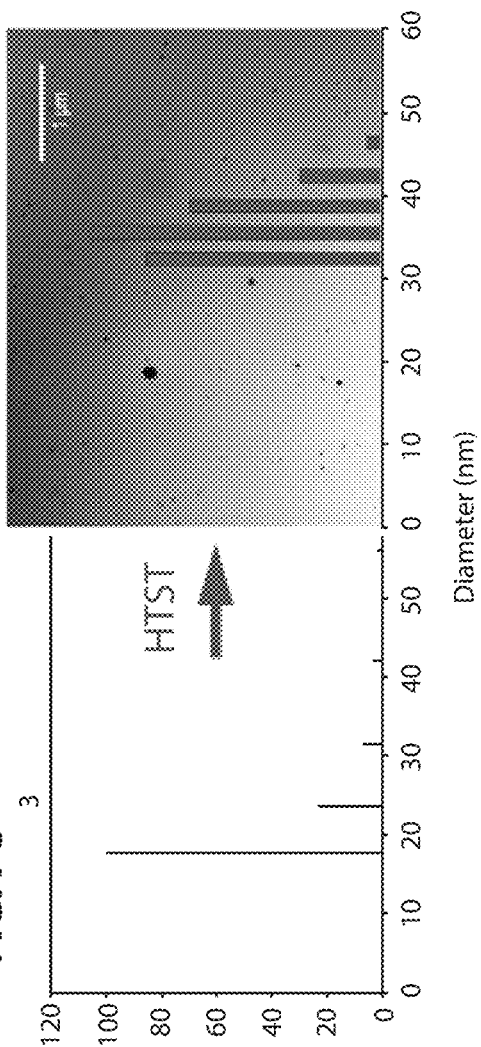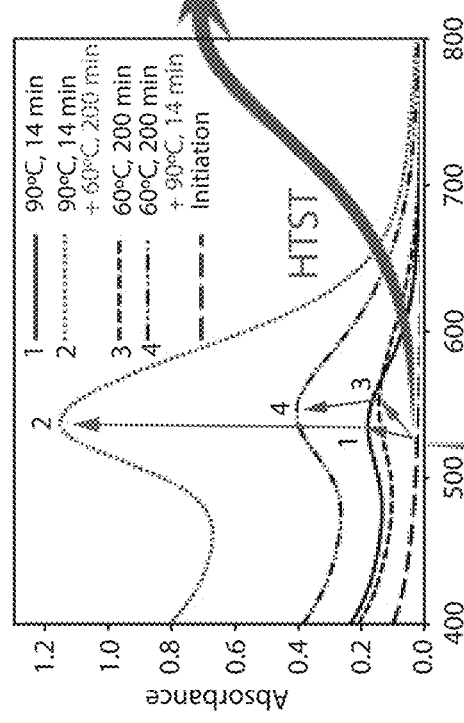
FIG. 7A • FIG. 7B • FIG. 7C

PACKAGING AND METHODS FOR DETECTING EXPOSURE OF A PERISHABLE GOOD TO AN ELEVATED TEMPERATURE

CROSS-REFERENCE TO RELATED APPLICATIONS

This application is a continuation of U.S. application Ser. No. 13/209,947, filed Aug. 15, 2011, now abandoned, which claims the benefit of priority of U.S. Provisional Application No. 61/374,127, filed Aug. 16, 2010, both of which are incorporated by reference herein in its entirety for any purpose.

FIELD AND BACKGROUND

This invention relates to packaging for a perishable good to monitor whether the perishable good was exposed to an elevated temperature during transit or storage. The perishable good is packaged, suitably within a container, with a system reactive to temperature changes comprising a metal precursor and a biopolymer carrier in a solvent.

Many products used by consumers and businesses are subject to quality-degrading effects. Quality degradation may be due simply to aging or to environmental stress, e.g., in handling, transport, storage and in the hands of the consumer. Such products include food, pharmaceuticals, biologics, polymeric products, chemical products, and the like. Prematurely degraded products can pose health and safety risks to consumers, and monetary loss to businesses.

The need for quality monitoring of many kinds of materials and products has become increasingly important for both safety and economic reasons. Certain quality-degrading micro-environmental factors, such as gas composition and relative humidity, can be fairly well-controlled through packaging. However, the effects of temperature and time can be difficult to control. Thermal stress combined with time can cause spontaneous changes in materials. Thus, it is frequently beneficial to provide an indicator or sensor of whether a product or material has been exposed to an undesirable time-temperature history which results in substantial degradation of the product or material.

SUMMARY

In some embodiments, a nanoreactor comprising a metal precursor and a carrier in a solvent is provided. In some embodiments, the metal precursor is selected from gold, silver, platinum, palladium, copper, and nickel ions. In some embodiments, the carrier is a biopolymer. In some embodiments, the carrier is gelatin. In some embodiments, the metal precursor is gold ions.

In some embodiments, the metal precursor is present at a concentration of between 0.1 mM and 5 mM. In some embodiments, the metal precursor is present at a concentration of between 0.2 mM and 3 mM. In some embodiments, the metal precursor is present at a concentration of between 0.5 mM and 2 mM. In some embodiments, the metal precursor is present at a concentration of between 0.5 mM and 1.5 mM. In some embodiments, the metal precursor is present at a concentration of 0.1 mM.

In some embodiments, the carrier is present at a concentration of between 0.01 g/mL and 0.1 g/mL in the solvent. In some embodiments, the carrier is present at a concentration of between 0.01 g/mL and 0.05 g/mL in the solvent. In some embodiments, the carrier is present at a concentration of between 0.01 g/mL and 0.03 g/mL in the solvent. In some embodiments, the carrier is present at a concentration of 0.02 g/mL in the solvent.

In some embodiments, a nanoreactor does not comprise an additional reducing agent.

In some embodiments, a nanoreactor system is provided. In some embodiments, a nanoreactor system comprises a nanoreactor in a container.

In some embodiments, a method of detecting exposure of a perishable good to elevated temperature by detecting formation of nanoparticles in the nanoreactor or detecting a change in a characteristic of the nanoreactor after such exposure is provided. In some embodiments, a method comprises detecting the presence of nanoparticles in the nanoreactor or detecting a characteristic of the nanoreactor in a nanoreactor system that is associated with the perishable good. The nanoreactor system can be associated with the perishable good by being included in a container with one or more unit of the perishable good, anchored to a container holding one or more units of the perishable good or otherwise present in a location that the nanoreactor and the perishable good are expected to experience similar environments.

In some embodiments, a method of monitoring the progress of an exothermic reaction is provided. In some embodiments, the method comprises detecting the presence of nanoparticles in a nanoreactor or detecting a change in a characteristic of the nanoreactor in a nanoreactor system that is associated with the reaction.

In some embodiments, detecting the presence of nanoparticles comprises detecting a characteristic of the nanoreactor selected from color, peak wavelength, peak shape, absorbance, nanoparticle size, nanoparticle size distribution, and nanoparticle number. In some embodiments, detecting the presence of nanoparticles comprises detecting the color of the nanoreactor by colorimetry or spectrophotometry. In some embodiments, the color of the nanoreactor is determined by visual inspection and comparison to a standard. In some embodiments, detecting the presence of nanoparticles comprises detecting at least one of the peak wavelength and the absorbance of the nanoreactor. In some embodiments, detecting at least one of the peak wavelength and the absorbance of the nanoreactor is carried out using a UV-Vis spectrophotometer. In some embodiments, detecting the presence of nanoparticles comprises detecting at least one of nanoparticle size, nanoparticle size distribution, and nanoparticle number. In some embodiments, detecting at least one of nanoparticle size, nanoparticle size distribution, and nanoparticle number is carried out using at least one of scanning electron microscopy (SEM), transmission electron microscopy (TEM), x-ray radiography, dynamic laser scattering (DLS), digital image processing (DIP), and atomic force microscopy (AFM).

In some embodiments, a method comprises comparing the characteristic to a standard.

In some embodiments, the perishable good is a perishable biologic. In some embodiments, the reaction is fermentation.

BRIEF DESCRIPTION OF THE FIGURES

This patent or application file contains at least one drawing executed in color. Copies of this patent or patent application publication with color drawings will be provided by the United States Patent Office upon request and payment of the necessary fee.

FIG. 2A shows a gelatin/gold nanoreactor immediately after mixing the gelatin and gold precursor. FIG. 2B shows a gelatin/gold nanoreactor after incubation at 277K for 1 month in the dark. FIG. 2C shows a gelatin/gold nanoreactor after incubation at 353K for 100 minutes, followed by incubation at 277K for 1 day.

FIG. 5A shows the change in peak wavelength at 10 minute intervals (20 minutes for 333K), starting with the first detectable peak value. FIG. 5B shows a comparison of the UV-Vis spectra of gelatin/gold nanoreactors incubated at different temperatures and times. Inset shows the color appearance of each of the samples whose spectrum is shown.

FIGS. 6A and 6C show the particle size distribution (A) and transmission electron micrograph (C) of the particles in a gelatin/gold nanoreactor incubated at 363K for 30 min. FIGS. 6B and 6D show the particle size distribution (B) and transmission electron micrograph (D) of the particles in a gelatin/gold nanoreactor incubated at 333K for 480 min.

FIGS. 7A-C show the UV-Vis spectra (A) and particle distribution (B and C) of gelatin/gold nanoreactors incubated under varying conditions, as described in Example 6.

DETAILED DESCRIPTION

Figure 1:
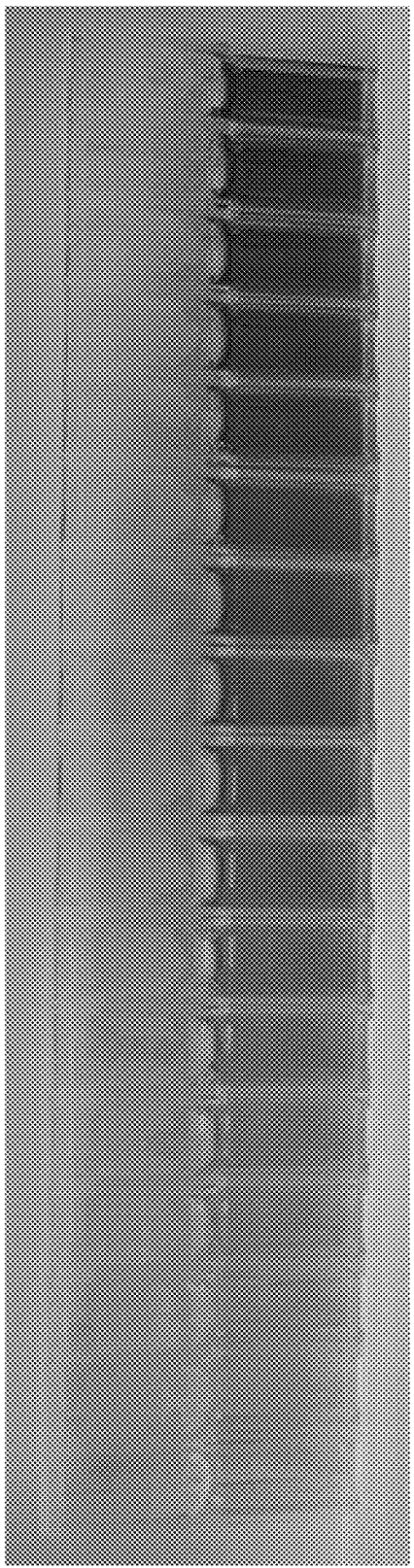
FIG. 1 shows a photograph of changes in intensity of the color of gelatin/gold nanoreactors as a function of time (10 min intervals) at 80° C.

The process of metal nanoparticle synthesis occurs through a balance of nucleation, growth, and aggregation. Further, the evolving attributes of nanoparticles during their formation can be used to indicate the conditions under which they were formed. Such attributes include, but are not limited to, the color of the nanoreactor solution in which the nanoparticles are formed, the peak wavelength and peak absorption of the nanoreactor solution, the size, shape, and number of nanoparticles, and the size distribution of the nanoparticles.

By using functional biopolymers (such as proteins and polysaccharides) as mediator materials for nanoparticle formation, nanoparticle formation can indicate certain changes in biologics. Further, since oxidation is a common cause of such changes in biologics, nanoparticle formation induced by natural oxidation of a biopolymer is a particularly good mimic for those changes.

An exemplary biopolymer that may be used in such a nanoreactor is gelatin, which is an edible protein derived from collagen. Due to its low cost and ability to form a thermo-reversible hydrogel, gelatin is used in a myriad of practical applications. Further, gelatin is particularly well suited because it is both a reducing agent and a stabilizer. Accordingly, as gelatin is naturally oxidized, it reduces the metal precursor in the nanoreactor, inducing nanoparticle formation. Gelatin then serves to stabilize the nanoparticles once formed. In addition, the transparency of gelatin allows the visual detection of color changes in a nanoreactor.

Accordingly, nanoreactors comprising a metal precursor and a carrier are provided. In some embodiments, nanoreactors comprising a metal precursor and a biopolymer carrier are provided. In some embodiments, nanoreactors comprising a metal precursor and gelatin are provided. In some embodiments, nanoreactors comprising gold precursor and gelatin are provided. In addition, methods of using nanoreactors to detect exposure of perishable goods to elevated temperature are provided.

Definitions

The term "metal precursor," as used herein, refers to a metal ion capable of nanoparticle formation under reducing conditions. In some embodiments, a metal precursor is a metal ion salt capable of temperature-induced nanoparticle formation under reducing conditions. Nonlimiting exemplary metal precursors include gold ions, silver ions, platinum ions, palladium ions, copper ions, and nickel ions. In some embodiments, a metal precursor is a mixture of two or more metal ions. Nonlimiting exemplary metal precursor mixtures include Au ion and Ni ion mixtures; Au ion and Ag ion mixtures; Au ion, Ag ion, and Cu ion mixtures; Au ion and Cu ion mixtures; Au ion and Pt ion mixtures; Fe ion, Co ion, and Ni ion mixtures, Ni ion and Cu ion mixtures; Ag ion and Pd ion mixtures; Fe ion and Co ion mixtures; and Pt ion and Ir ion mixtures. In some embodiments, a metal precursor is a "color-changing metal precursor," which refers to a metal precursor that is a first color, or no color, in solution, and which can form nanoparticles under certain reducing conditions, wherein the nanoparticles are a second color in solution. In some embodiments, the first color is no color (i.e., the metal precursor does not contribute to the color of the solution, so the solution may be clear). In some embodiments, the second color varies depending on the temperature at which the nanoparticles are formed. A nonlimiting exemplary color-changing metal precursor is gold precursor, gold-silver mixture (AuAg), and silver precursor.

The term "metal precursor salt," as used herein, refers to a salt of a metal precursor. A metal precursor salt may be a solid salt that can be dissolved in an appropriate solution. Once dissolved, the metal precursor salt separates into a metal precursor (or ion) and a counterion or counterions. Nonlimiting exemplary metal precursor salts include $HAuCl_4$, $KAuCl_4$, $NaAuCl_4$, $KAuCl_4$, and $AuCl_3$. In some embodiments, a metal precursor salt is a "color-changing metal precursor salt." Nonlimiting exemplary color-changing metal precursor salts include $HAuCl_4$, $KAuCl_4$, $NaAuCl_4$, $KAuCl_4$, and $AuCl_3$.

The term "carrier," as used herein, refers to a polymer that is (a) capable of acting as a reducing agent, and (b) capable of stabilizing nanoparticles. In some embodiments, a carrier has a high capacity for holding soluble metal ions. In some embodiments, a carrier is capable of preventing or reducing aggregation of nanoparticles. In some embodiments, a carrier is capable of forming a gel. In some embodiments, a carrier comprises sulfur-containing substituents, such as thiols. In some embodiments, a carrier is a biopolymer. A nonlimiting exemplary biopolymer that is suitable for use as a carrier is gelatin.

The term "gelatin," as used herein, refers to a protein produced by denaturation of collagen, and derivatives of the protein produced by denaturation of collagen that retain the ability to (a) act as a reducing agent and (b) stabilize nanoparticles. Gelatin includes, but is not limited to, type A gelatin and type B gelatin. Gelatin may be derived from any suitable source of collagen, and from any suitable organism. Nonlimiting exemplary sources of gelatin include bovine, porcine, ovine, equine, and piscine.

The term "nanoreactor," as used herein, refers to a composition comprising a metal precursor and a carrier. In some embodiments, a nanoreactor comprises a metal precursor and gelatin. In some embodiments, a nanoreactor comprises a gold precursor and gelatin.

The term "nanoreactor system," as used herein, refers to a nanoreactor that is encased such that it is suitable for inclusion with, or in, a perishable good. In some embodiments, a nanoreactor system is encased in such a way that the presence of nanoparticles in the nanoreactor system can be detected without opening the system. In some embodiments, a nanoreactor system is encased in such a way as to facilitate the removal of a sample of the nanoreactor for detection of nanoparticles.

The term "perishable good," as used herein, refers to an item or product that is negatively affected by temperatures above the acceptable storage temperature for the perishable good. The term "negatively affected" means that the good becomes less suitable for the use for which it is intended. Nonlimiting exemplary ways in which a good may become less suitable include degradation, loss of potency, weakening, change in color, change in consistency, precipitation from solution, denaturation, and loss of viability. Exemplary perishable goods include, but are not limited to, food (including solid and liquid foods), pharmaceuticals, biologics, polymeric goods (such as rubbers, vinyls, polyesters, plastics, etc.), petroleum products (such as engine oil, etc.), fabrics (including linen, cotton, leather, etc.).

The term "perishable biologic," as used herein, refers to biologic goods that are negatively affected by elevated temperatures. Biologic goods include, but are not limited to, proteinaceous therapeutics, such as antibodies, proteins, and peptides; vaccines; blood and blood components; cells; tissues; organs; and clinical and medical samples, such as blood and blood components, cells, tissues, organs, biopsy tissue, bodily fluids, etc.

The term "elevated temperature," as used herein, refers to a temperature above the acceptable storage temperature of a perishable good. Thus, if the acceptable storage temperature of a perishable good is 4° C. to 10° C., an elevated temperature is a temperature above 10° C. If the acceptable storage temperature of a perishable good is between 20° C. and 30° C., an elevated temperature is a temperature above 30° C. In the Examples, elevated temperatures of 60° C., 70° C., 80° C. and 90° C. were used as elevated temperatures and 4° C. was used as the base or storage temperature.

The term "exothermic reaction," as used herein, refers to a reaction or process that emits heat. A nonlimiting exemplary exothermic reaction is fermentation.

Exemplary Nanoreactors

In some embodiments, nanoreactors are provided. A nanoreactor comprises a metal precursor and a carrier. In some embodiments, the metal precursor and carrier are dissolved in water. In some embodiments, the metal precursor is present in the nanoreactor at a concentration of between 0.1 mM and 5 mM, or between 0.2 mM and 3 mM, or between 0.5 mM and 2 mM, or between 0.5 mM and 1.5 mM, inclusive of the endpoints. In some embodiments, the metal precursor is present in the nanoreactor at a concentration of 0.5 mM, 0.6 mM, 0.7 mM, 0.8 mM, 0.9 mM, 1.0 mM, 1.1 mM, 1.2 mM, 1.3 mM, 1.4 mM, or 1.5 mM.

In some embodiments, the carrier is present in the nanoreactor at a concentration of between 0.01 g/mL and 0.1 g/mL of solution, or between 0.01 g/mL and 0.07 g/mL, or between 0.02 g/mL and 0.05 g/mL, inclusive of the endpoints. In some embodiments, the carrier is present in the nanoreactor at a concentration of 0.01 g/mL, 0.015 g/mL, 0.02 g/mL, 0.025 g/mL, 0.03 g/mL, 0.035 g/mL, 0.04 g/mL, 0.045 g/mL, or 0.05 g/mL of solution.

In some embodiments, the concentration of metal precursor/concentration of carrier is 1 mM/0.02 g/mL; 1 mM/0.05 g/mL; 0.5 mM/0.02 g/mL, or 1.15 mM/0.02 g/mL of solution.

In some embodiments, the metal precursor is gold precursor and the carrier is gelatin. In some embodiments, gold precursor in the nanoreactor comes from dissolving a gold salt selected from $HAuCl_4$, $KAuCl_4$, $NaAuCl_4$, $KAuCl_4$, and $AuCl_3$ in the nanoreactor.

In some embodiments, a nanoreactor does not comprise an additional reducing agent. The term "additional reducing agent," as used herein, means a reducing agent that is added to the nanoreactor, other than the carrier. Nonlimiting exemplary additional reducing agents include trisodium citrate with or without sodium 3-mercaptopropionate, alkane thiols, polythioethers, xanthates, disulfides, dithiols, trithiols, dithiothreitol (DTT), β-mercaptoethanol, $N_2H_4$, etc.

Exemplary Nanoreactor Systems

In some embodiments, a nanoreactor is part of a nanoreactor system. A nanoreactor system comprises a nanoreactor encased such that it is suitable for inclusion with or in a perishable good. Nonlimiting exemplary nanoreactor systems include nanoreactors in containers made from, for example, glass, plastic, quartz, metal, micelles, liposomes, membranes, gels (such as agar), etc.

In some embodiments, a nanoreactor system is designed such that characteristics of the nanoreactor or nanoparticles forming in the nanoreactor can be detected without opening the nanoreactor system. For example, if the nanoreactor will be detected visually, e.g., by observing a color change, the nanoreactor system container will not interfere with the visual detection. In some such embodiments, the nanoreactor container is translucent, for example, it is made from glass, clear plastic, or quartz. In some embodiments, the nanoreactor system container is clear (i.e., lacking detectable color). In some embodiments, the nanoreactor system container is colored, but translucent. In some such embodiments, the color of the nanoreactor system container does not interfere with the visual detection of the nanoparticle generation in the nanoreactor, or even enhances the visual detection.

In some embodiments, a nanoreactor system is designed such that nanoparticles can be detected in the nanoreactor through other means without opening the nanoreactor system. For example, in some embodiments, the formation of nanoparticles is detected using x-ray radiography. In some such embodiments, the nanoreactor system container does not interfere with detection by x-ray radiography. That is, in some such embodiments, the nanoreactor container is not made of a material that blocks x-rays, such as lead.

In some embodiments, a nanoreactor system is designed such that a sample can be taken from the nanoreactor system for detection of nanoparticle formation. In some such embodiments, the nanoreactor system container includes a portion that can be opened for collection of a sample. After opening, the nanoreactor system container can either be resealable or non-resealable. In some embodiments, the nanoreactor system includes a cartridge or other removable portion that contains at least a sample of the nanoreactor. In some embodiments, the cartridge or other removable portion is suitable for detecting nanoparticles in the nanoreactor by a selected method.

In some embodiments, a sample of the nanoreactor is removed from the nanoreactor system for detection by a selected method. Such removal may be by any suitable method, including pipetting, pouring, capillary action, etc. In some embodiments, a nanoreactor system includes a device for facilitating removal of a sample of the nanoreactor. Nonlimiting exemplary devices include pipets, capillaries, adaptors for transferring the nanoreactor from the system to the detection device, etc.

In some embodiments, a nanoreactor system is disposable.

Exemplary Methods of Detecting Nanoparticles Formed in Nanoreactors

Detection of nanoparticles formed in nanoreactors may be by any suitable method. Further, detection of nanoparticles may be through detection of any characteristic of the nanoparticles and/or the nanoreactor, such as color, peak wavelength, peak absorbance, shape of the absorbance peak(s), nanoparticle size, nanoparticle shape, nanoparticle size distribution, number of nanoparticles, etc.

Exemplary detection methods include, but are not limited to, visible inspection, UV-Vis spectrophotometry, scanning electron microscopy (SEM), transmission electron microscopy (TEM), dynamic laser scattering (DLS), x-ray radiography, digital image processing (DIP), and atomic force microscopy (AFM).

In some embodiments, when the characteristic to be detected is color, visual inspection and/or UV-Vis spectrophotometry is selected as a detection method.

In some embodiments, when the characteristic to be detected is peak wavelength and/or peak absorbance and/or peak shape, UV-Vis spectrophotometry is selected as a detection method. In some embodiments, when a peak wavelength and/or peak absorbance and/or peak shape is to be detected and the nanoreactor comprises gold nanoparticles, a spectrum that includes at least 530 nm to 550 nm is taken. In some embodiments, a spectrum from 400 nm to 800 nm is taken.

In some embodiments, the absorbance of one ore more individual wavelengths are determined. In some such embodiments, at least one wavelength is a wavelength between 530 nm and 550 nm. In some such embodiments, at least one wavelength is selected from 530, 531, 532, 533, 534, 535, 536, 537, 538, 539, 540, 541, 542, 543, 544, 545, 546, 547, 548, or 550 nm.

In some embodiments, when the characteristic to be detected is nanoparticle size, suitable detection methods include, for example, DLS, SEM, TEM, AFM, x-ray radiography, and digital image processing (DIP) of the images obtained from, e.g., SEM and TEM.

In some embodiments, when the characteristic to be detected is nanoparticle shape, suitable detection methods include, for example, SEM, TEM, AFM, UV-visible spectroscopy, x-ray radiography, and DIP of the images obtained from, e.g., SEM and TEM.

In some embodiments, when the characteristic to be detected is nanoparticle number, suitable detection methods include, for example, DLS and x-ray radiography.

In some embodiments, when the characteristic to be detected is nanoparticle size distribution, suitable detection methods include, for example, DLS and x-ray radiography.

One skilled in the art can select a suitable detection method depending on the characteristic(s) of the nanoreactor and/or nanoparticles that are to be detected. The selected method need not be a method specifically listed above.

In some embodiments, a detection method includes the use of a standard. The discussion below provides nonlimiting exemplary standards that may be suitable. One skilled in the art can devise a suitable standard according to the particular detection method, detection location, user, nanoreactor system, use of the nanoreactor system, etc.

When the detection method is visual inspection of nanoreactor color, in some embodiments, a standard may comprise one ore more colors to which the color of the nanoreactor can be compared. The one or more color standards may be in any form, such as colors printed on paper, plastic, cardstock, etc.; or colored samples that have a similar appearance to the nanoreactor. By "similar appearance," it is meant, in some embodiments, that the samples have similar viscosity and/or opacity and/or are packaged in similar containers as the nanoreactor. The samples, in some embodiments, are not themselves nanoreactors, but samples that mimic the appearance of a nanoreactor that has been exposed to certain time/temperature conditions. In some embodiments, a color standard comprises more than one color such that a nanoreactor can be compared to the color standard and by identifying the color closest to the color of the nanoreactor, the time/temperature conditions experienced by the nanoreactor can be estimated.

When the detection method is UV-Vis spectrophotometry, in some embodiments, a standard may be one or more samples that produce similar spectra as nanoreactors that have experienced various time/temperature conditions. In some embodiments, a standard may be a document showing one or more peak wavelengths and/or peak absorbances of nanoreactors that have experienced certain known time/temperature conditions.

With any detection method, a standard comprising a known number, shape, size, and/or size distribution of nanoparticles may be used and the nanoreactor compared to the known standards. In some embodiments, a standard is generated by subjecting a nanoreactor to particular conditions, such as in a laboratory. In some embodiments, one or more characteristics of the nanoreactor and/or nanoparticles of the standard are detected using one or more methods described above. In some embodiments, the output of that detection is then used as standard. That is, for example, in some embodiments, a UV/visible spectrum taken of a standard nanoreactor subjected to particular conditions is used as standard against which UV/visible spectra of nanoreactors in use are compared. In some embodiments, multiple standards are used. In some embodiments, when multiple standards are used, one or more of the multiple standards are based on nanoreactors that have been subjected to different particular conditions. In some embodiments, when multiple standards are used, one or more of the multiple standards show different characteristics of one or more nanoreactors that have been subjected to different particular conditions. One skilled in the art can select a suitable standard according to the intended use of the nanoreactors.

Exemplary Methods of Using Nanoreactors

Methods of using nanoreactors to detect exposure of a perishable good to elevated temperature are provided. Such methods comprise, in some embodiments, detecting nanoparticles in a nanoreactor that is associated with the perishable good. Methods of using nanoreactors to monitor an exothermic reaction are also provided. Such methods comprise, in some embodiments, detecting nanoparticles in a nanoreactor that is associated with the reaction.

Figure 8A:
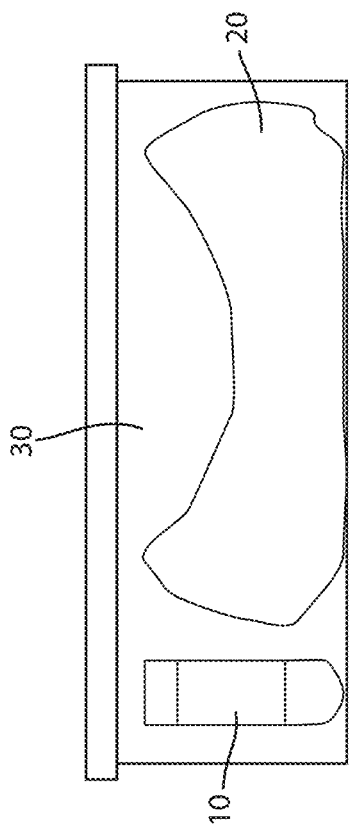
FIGS. 8A-C show several ways the nanoreactor system can be associated with a perishable good or the container holding one or more perishable goods.
Figure 8B:
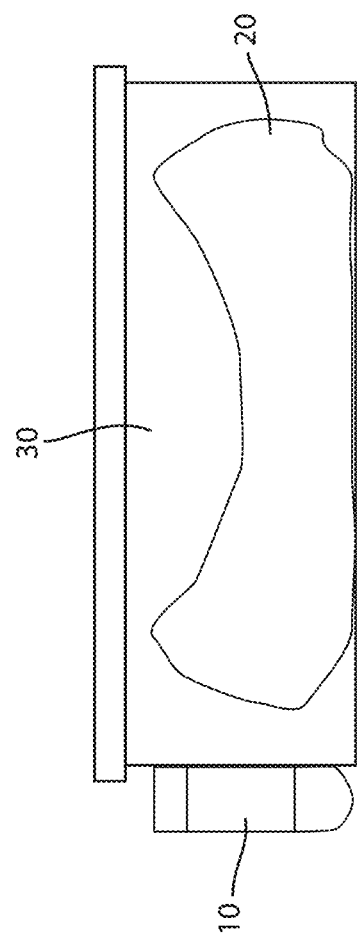
Figure 8C:
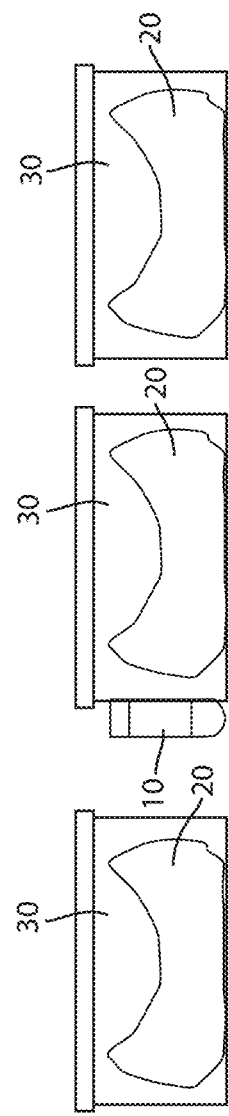

As shown in FIG. 8, a nanoreactor system 10 is associated with a perishable good 20 when it is included within the packaging 30 of the perishable good, included in a container 30 with one or more units of the perishable good 20 (FIG. 8A), anchored to a container 30 holding one or more units of the perishable good 20 (FIG. 8B and FIG. 8C), or otherwise present in such a location that the nanoreactor system 10 is expected to experience a similar environment as the perishable good 20. In some embodiments, a similar environment is a similar temperature environment. In some embodiments, a container 30 holds multiple smaller containers, each of which holds multiple units of the perishable good 20. In some such embodiments, a nanoreactor system 10 can be associated with a unit of the perishable good 20, with the smaller container 30, or with the container holding multiple smaller containers. That is, the nanoreactor system 10 may be included in (FIG. 8A), or anchored to (FIG. 8B), a unit of the perishable good, such as in a box in which the perishable good is provided to consumers; or it may be included in, or anchored to, a container holding multiple units of the perishable good; or it may be included in, or anchored to, a container holding multiple such smaller containers that hold multiple units of the perishable good, etc. (FIG. 8C).

In some embodiments, a nanoreactor is included in the same container as the perishable good. For example, in some embodiments, a nanoreactor system is included inside a glass or plastic container that also holds the perishable good. See FIG. 8A. In some such embodiments, the nanoreactor system is visible through a wall of the glass or plastic container. In some embodiments, whether or not the nanoreactor system is visible, it is present in a known location such that microparticles in the nanoreactor system can be detected by a particular method without opening the container that holds the perishable good.

Similarly, in some embodiments, a nanoreactor is included in the same container as an exothermic reaction to be monitored, or in a location in close enough proximity to the reaction such that the nanoreactor is exposed to at least a portion of the heat emitted by the exothermic reaction.

In some embodiments, the presence of nanoparticles in the nanoreactor can be detected after first removing the nanoreactor system from the location where it is (or was) associated with the perishable good or reaction (the perishable good or reaction need not still be present at the time the nanoreactor system is removed and detected). In some embodiments, the detection is done in situ—from the location where it is (or was) associated with the perishable good or reaction (again, the perishable good or reaction need not still be present at the time the nanoreactor system is detected).

In some embodiments, the location of the nanoreactor system that is associated with a perishable good or reaction is known such that nanoparticles in the nanoreactor can be detected without first removing the nanoreactor or nanoreactor system from the location where it is (or was) associated with the perishable good or reaction. As a nonlimiting example, a nanoreactor system may be anchored to the inside of a container holding the perishable good or reaction. In some embodiments, the location of the nanoreactor system is known and/or indicated on the outside of the container. Nanoparticles in the nanoreactor system can be detected, e.g., using x-ray radiography even though the nanoreactor system is not visible to an outside observer.

The presently described nanoreactors provide a way of detecting exposure of a perishable good to elevated temperature. The presently described nanoreactors also provide a way of monitoring the progress of an exothermic reaction. The color (i.e. hue and/or intensity), peak wavelength, and/or peak absorbance of the nanoreactor; as well as the size, number, size distribution and/or shape of the nanoparticles formed in the nanoreactor, provide information on the temperature to which the nanoreactor has been exposed, and the duration of the exposure to that temperature.

As a nonlimiting example, if the nanoparticles are being detected visually, a more reddish hue indicates exposure to higher temperature, while a more purple hue (i.e., a shift from red towards blue) indicates exposure to lower temperature. See, e.g., FIG. 5. Further, the greater the intensity of the hue, the longer the exposure to that temperature. If the nanoparticles are being detecting using UV-Vis spectroscopy, lower peak wavelengths indicate exposure to high temperature, while higher peak wavelengths indicate exposure to low temperature. Thus, in some embodiments, for a nanoreactor comprising 1 mM $HAuCl_4$ and 0.02 g/mL gelatin, a peak wavelength of 535 nm indicates exposure to 90° C., a peak wavelength of 537 nm indicates exposure to 80° C., a peak wavelength of 540 nm indicates exposure to 70° C., and a peak wavelength of 546 nm indicates exposure to 60° C. Further, the absorbance at the peak wavelength indicates the length of time during which the nanoreactor was exposed to that temperature, up to a maximum value that is determined by the concentration of metal precursor available in the nanoreactor. Thus if the nanoreactor is associated with a perishable good, detecting exposure of the nanoreactor to these elevated temperatures for lengths of time can be inferred to similar exposure of the perishable good to similar temperatures for similar lengths of time.

In addition, the breadth of the peak detected by UV-Vis spectroscopy is also indicative of the temperature to which the nanoreactor has been exposed. In some embodiments, a broader (i.e., wider) peak, with greater absorbance in the 650 nm to 700 nm range, indicates exposure to lower temperature, while a narrower peak, with a steeper slope up to 650 nm, indicates exposure to higher temperature.

If the nanoparticles are being detected using a method that detects the number, size, size distribution and/or shape of the nanoparticles, a higher number of smaller particles that are more uniform in size and shape indicates exposure to higher temperature, while a lower number of larger particles that are less uniform in size and shape indicates exposure to lower temperature. Thus, in some embodiments, for a nanoreactor comprising 1 mM $HAuCl_4$ and 0.02 g/mL gelatin, a large number of nanoparticles that are less than 10 nm in size indicates exposure to, for example, 90° C. for a shorter time, such as 30 minutes. See, e.g., FIG. 5. In contrast, in some embodiments, a lower number of larger nanoparticles, ranging in size from about 45 nm to over 100 nm, indicates exposure to, for example, 60° C. for a longer time, such as 480 minutes. See id.

In some embodiments, when a nanoreactor is included in a perishable good, the nanoreactor may be accompanied by instructions to the recipient of the perishable good, such as a distributor, seller, and/or consumer, on how to interpret the nanoreactor. In some embodiments, the instructions will provide a reference to which a characteristic of the nanoreactor can be compared. In some embodiments, the reference will comprise one or more colors to which the color of the nanoreactor can be compared. In some embodiments, the instructions will include instructions to notify an originator of the perishable good, such as a manufacturer, distributor, and/or seller, in the event the nanoreactor has one or more particular characteristics and/or return the perishable good to an originator.

Further, in some embodiments, by using appropriate standards as discussed above, one skilled in the art can determine the temperatures to which a perishable good has been exposed, and estimate the duration of that exposure. Similarly, by using appropriate standards as discussed above, one skilled in the art can determine the progress of an exothermic reaction. However, the use of standards is not required to practice the present invention.

The following examples are offered by way of illustration and are not intended to limit the invention in any manner.

EXAMPLES

Example 1: Preparation of Nanoreactor

A gold precursor, powdered hydrogen tetrachloroaurate (HAuCl4, Fisher), was dissolved in deionized ("DI") water to prepare a 10 mM solution. A 0.022 g/mL solution of powdered gelatin (Acros, Type A) was prepared in DI water by dissolving the gelatin in the water in a 353K water bath with stirring for 30 min.

The gelatin solution was moved to an incubator set at the desired temperature and left for 15 min to reach equilibrium. The prepared HAuCl4 solution (10 mM) was preheated to the same temperature. After the solutions reached temperature equilibrium, a sufficient volume of 10 mM $HAuCl_4$ solution was injected into the gelatin solution to result in a final concentration of 1 mM $HAuCl_4$ in 0.02 mg/mL gelatin. Process time was measured from the time of $HAuCl_4$ solution injection.

Periodically, samples were collected, imaged, and tested for their optical properties through UV-visible spectra using a spectrophotometer (Shimadzu, UV-1500). For certain experiments, dynamic light scattering (DLS) analysis to determine particle size (Brookhaven Instruments Corporation, 90Plus) and/or transmission electron microscope analysis (TEM) (Philips, CM120 STEM) were also performed. Color characteristic of the gelatin/Au solution were also analyzed using a color histogram of a small pixel cubic centimeter (1×1 cm, 300 pixel/$cm^2$) cut from a picture of a sample taken at the same distance, using photo software (Adobe Photoshop 7).

Example 2: Formation of Gold Nanoparticles Upon Heating the Nanoreactor

Figure 3:
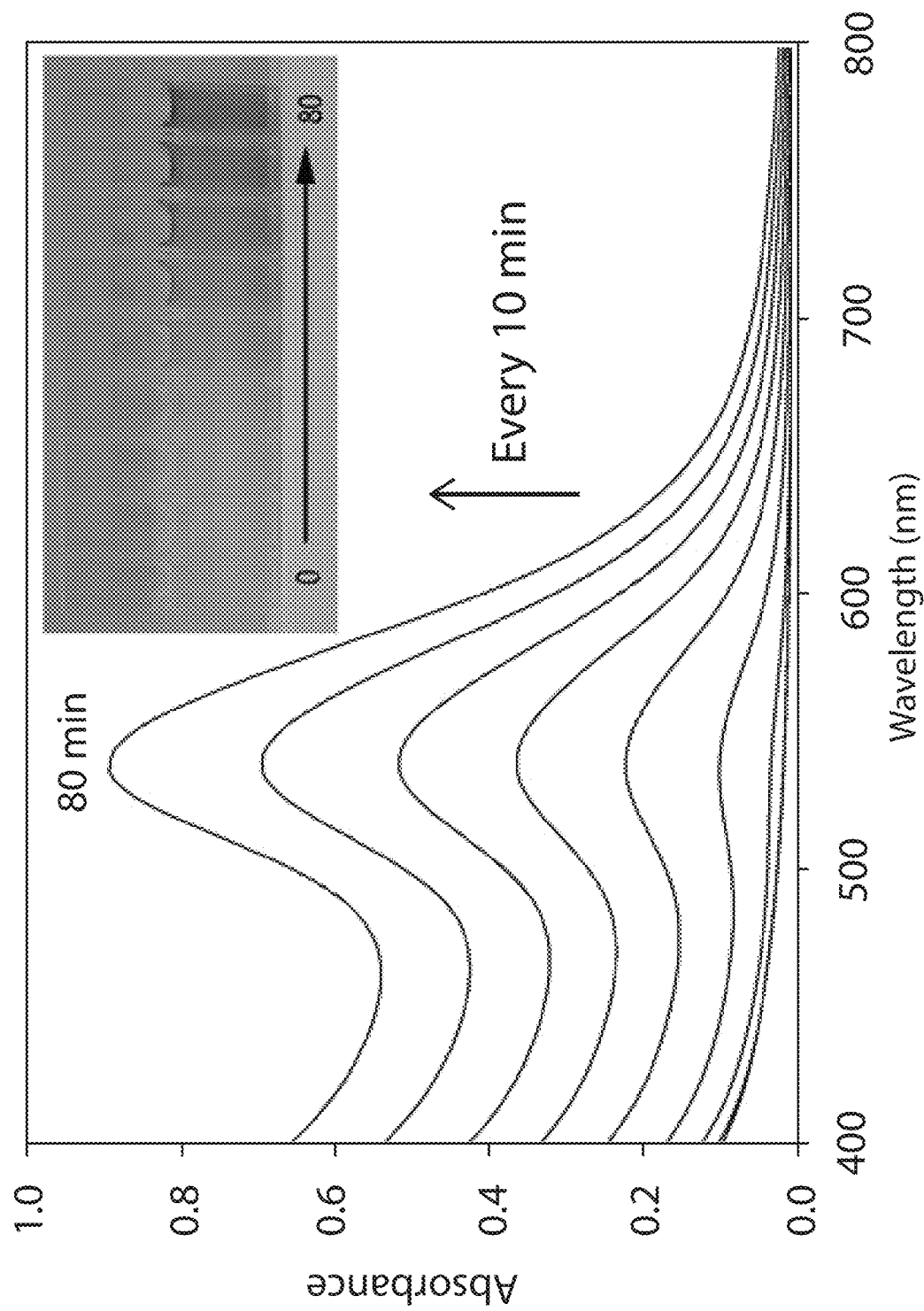
FIG. 3 shows UV-Vis absorption spectra of gelatin/gold nanoreactors incubated at 353 K, measured every 10 minutes for 80 minutes.

The color and intensity of AuNP nanoreactor system, prepared as described in Example 1 above (0.02 g/mL bovine gelatin; 1 mM $HAuCl_4$), was incubated at 80° C. (353 K) for three hours. As seen in FIG. 1, the intensity of red color steadily increased during the incubation period, demonstrating the increase in amount of gold nanoparticles. The UV-Vis spectrum (obtained on a Shimadzu UV-1500 UV-Vis spectrophotometer at 0.5 nm resolution from 400 to 800 nm) at each of those time points is shown in FIG. 3. The inset in FIG. 3 shows the color of the nanoreactor at each of the time points. Those data confirm that a proportional change in color intensity is observed over time.

The increasing intensity of the red color over time suggests an increase in the number of gold nanoparticles over time. See FIG. 3. The peak absorption wavelength remained constant, at 538 nm. Further, the low absorption values above 600 nm suggest that the nanoparticles are fairly spherical in shape and have a narrow size distribution.

Figures 2A, 2B, 2C:
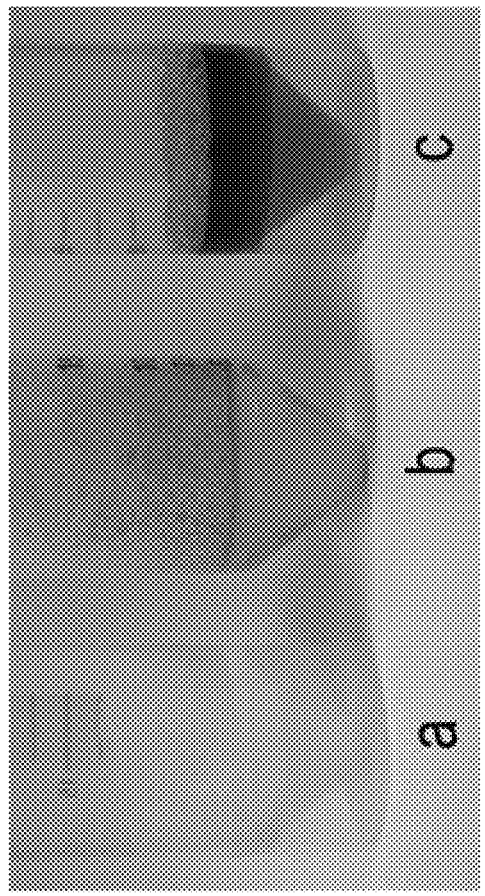
FIGS. 2A-C show gelatin/gold nanoreactors incubated under different conditions.

Example 3: Formation of Gold Nanoparticles Upon Storing and Heating the Nanoreactor A solution of 0.2 g/mL gelatin and 1 mM $HAuCl_4$ was prepared as described in Example 1 above. Time zero was set as the time when the $HAuCl_4$ and gelatin were brought together and mixed. FIG. 2A shows the nanoreactor immediately after mixing. FIG. 2B shows the nanoreactor after storage at 277K for 1 month. FIG. 2C shows the nanoreactor after incubation at 353K for 100 min, followed by storage at 277K for 1 day. The nanoreactor in FIG. 2C was also kept in the dark for the entire process.

The results in FIG. 2B suggest that nanoparticles are only formed at 277K where the system is in contact with air (i.e., in the bubbly portion of the nanoreactor only). FIG. 2C shows that nanoparticle formation occurs throughout the nanoreactor upon heating. Those results suggest that oxidation of gelatin occurs during formation of the gold nanoparticles.

Figure 4:
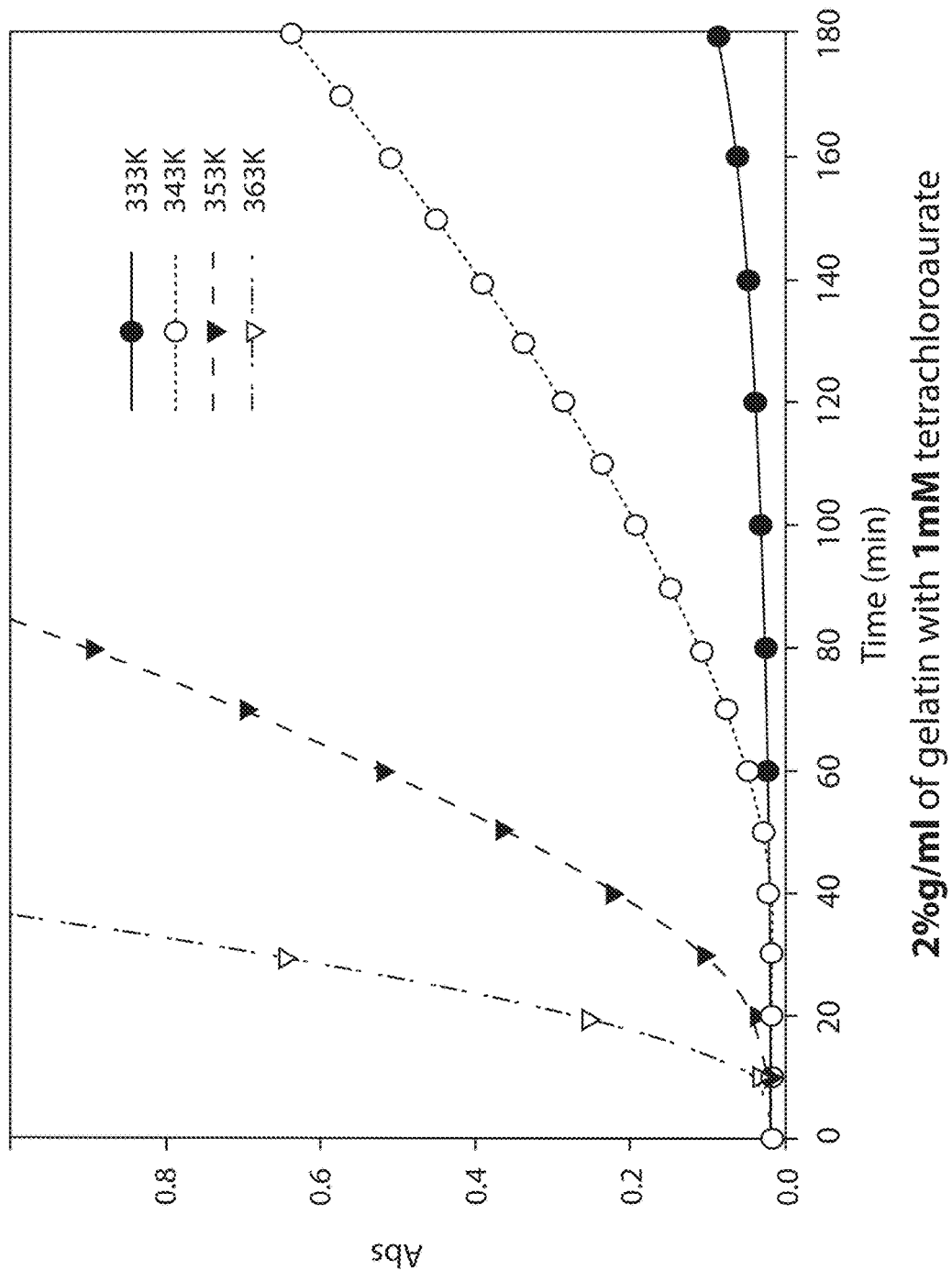
FIG. 4 shows the absorption at 538 nm of gelatin/gold nanoreactors at various temperatures as a function of time.

Example 4: Slope of Nanoreactor Absorption Versus Time Changes with Temperature Nanoreactors were prepared as described in Example 1. Nanoreactors were incubated at 333 K, 343 K, 353 K, or 363K. Samples were taken every ten minutes and the absorption at 538 nm determined. FIG. 4 shows a plot of the absorption versus time for the nanoreactors at each temperature. Those results suggest that the change in the rate of nanoparticle formation with temperature follows the Arrhenius equation. In addition, the lag time before nanoparticle formation begins, varied with temperature in that experiment.

Under isothermal conditions, the increase in intensity of reddish color is in proportion to reaction time. Since the oxidation of gelatin appears to drive nanoparticle synthesis, the relationship between the rate of nanoparticle synthesis and temperature may be attributable to the response of gelatin to temperature.

Example 5: Nanoreactor Peak Wavelength Changes with Temperature

Figure 5A:
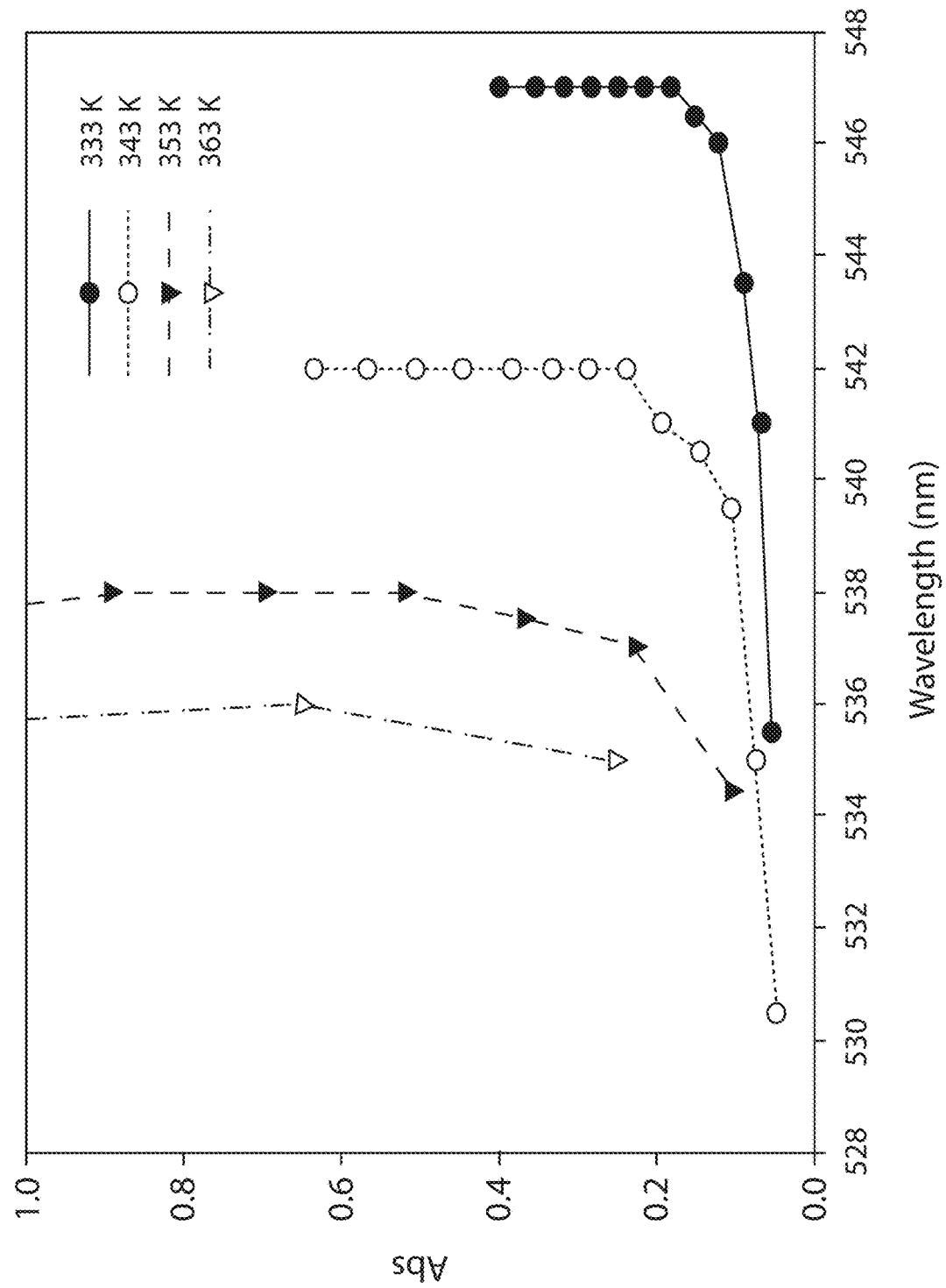
FIGS. 5A-B shows the change in peak wavelength of gelatin/gold nanoreactors incubated at various temperatures.

The UV-Vis spectrum of each sample from Example 4 was measured every ten minutes. As shown in FIG. 5A, not only does the rate of nanoparticle formation change with temperature (see Example 4), but the peak absorption wavelength of the nanoreactor also changes with temperature.

As can be seen in FIG. 5A, nanoreactors incubated at 333 K had a peak wavelength of about 547 nm, nanoreactors incubated at 343 K had a peak wavelength of 542 nm, nanoreactors incubated at 353 K had a peak wavelength of 538 nm, and nanoreactors incubated at 363 K had a peak wavelength of about 536 nm. Further, the rate at which the peak wavelength was reached increased with increasing temperature. In addition, the lag time seen in FIG. 4 appears to be related to the time it takes for the peak wavelength to be reached in FIG. 5A.

Figure 5B:
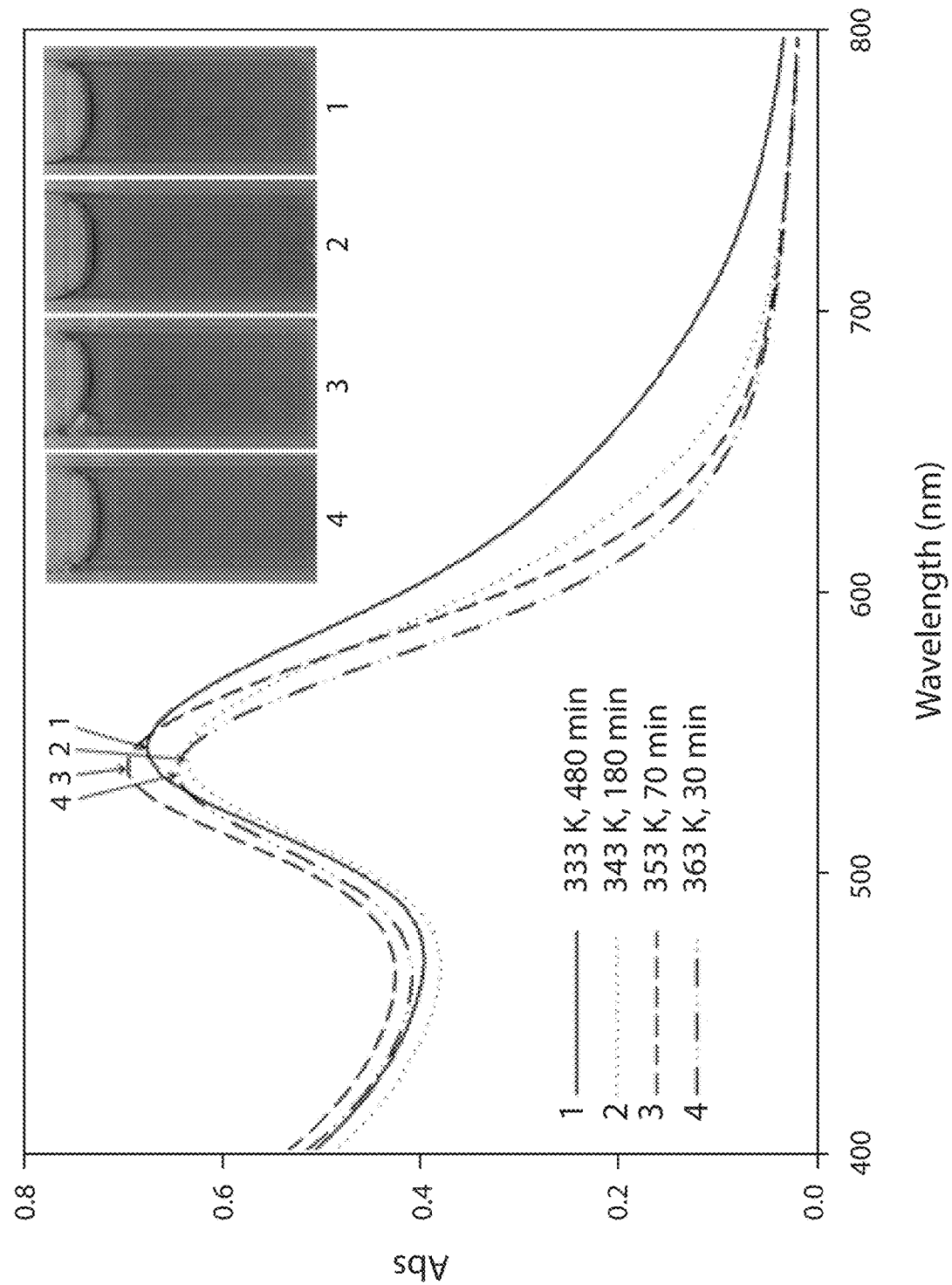

FIG. 5B shows the UV-Vis spectra of samples incubated at the four different temperatures, and showing the different peak wavelengths. Four samples were chosen that had similar peak intensities (333 K for 480 min., 343 K for 180 min., 353 K for 70 min., and 363 K for 30 min.). The inset shows the color of each of the samples, which shifts from reddish to purplish as the peak wavelength shifts from 536 nm to 547 nm.

The peak wavelength of UV-Vis spectra changes according to the size of the nanoparticles, while the peak absorption value changes according to the relative number of particles. See Sugimoto, *Chemical Engineering & Technology* 26, 313-321 (2003); Patakfalvi et al., *J. Nanopart. Res.* 9, 353-364 (2007). Thus, peaks appearing at higher wavelengths should be due to larger particles, which are formed in the nanoreactor at lower temperatures. Further, peak shifting from lower to higher wavelength during the reaction indicates growth of nanoparticles. See FIG. 5A. Considering that growth is a sequential process following nucleation and a certain minimum number and size of particles are needed to register in the UV-Vis spectra, the relationship between temperature and the slope of the peak shift reveals that at high temperature, relatively larger amounts of particles are formed by faster nucleation, with slower growth of each particle, resulting in smaller size. At lower temperature, the reverse is seen.

Further, in addition to the change in peak wavelength, the absorption at higher wavelengths also changed with temperature. That is, nanoreactors incubated at lower temperatures for longer times had higher absorbance at wavelengths above 600 nm. See FIG. 5B. The higher absorbance above 600 nm suggests the presence of larger nanoparticles. Further, absorption above 700 nm suggests a diversity of nanoparticle shape and possibly aggregation. See, e.g., Daniel et al., *Chem. Rev.* 104, 293-346 (2004); Ghosh et al. *Chem. Rev.* 107, 4797-4862 (2007); Yu et al. *J. Phys. Chem. B* 101, 6661-6664 (1997). Thus, it appears that at lower temperature, the larger nanoparticles are irregular in shape.

Example 6: Temperature Dependence of Gold Nanoparticle Number and Size Distribution Nanoreactors were prepared and incubated at either 363 K for 30 minutes, or 333 K for 480 minutes (see, e.g., samples 1 and 4 in Example 4). Samples of each nanoreactor were subjected to transmission electron microscopy, as follows. Samples were pipetted directly onto the platform support film coated with a 200-mesh Ni grid. After removing excess sample with filter paper, the samples were dried at room temperature for 1 hour and examined using a Philips CM120 STEM transmission electron microscope (80 kV) to determine the size distribution and shape of the nanoparticles. FIGS. 6C and 6D show the transmission electron micrographs of the nanoreactors incubated at higher temperature and lower temperature, respectively. Those figures show that nanoparticles produced at higher temperature are smaller and of more uniform size, while nanoparticles produced at lower temperature are larger and of more varied size.

The particle size distributions were then determined using dynamic laser light scattering (DLS) on a 90Plus Particle Size Analyzer equipped with a Peltier temperature control system (Brookhaven Instruments Corp., Holtsville, N.Y.). The measurements were collected at a fixed 90° C. angle and a wavelength of 659 nm. Samples of the nanoreactors were equilibrated to process temperature before each particle size measurement. Three replicate measurements were performed for each experimental condition. Each measurement consisted of five individual runs of 30 second duration.

Figure 6A:
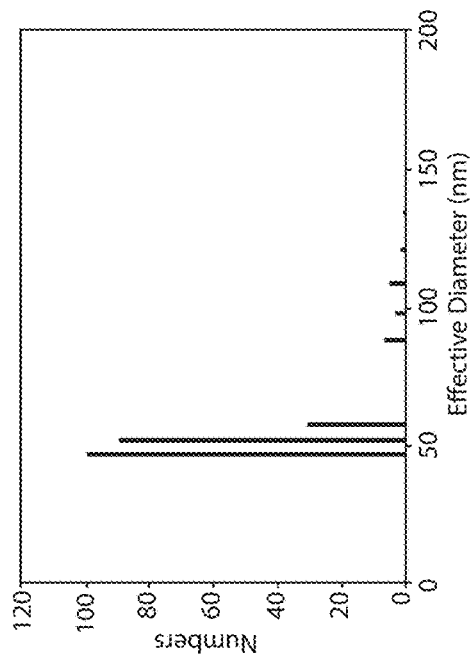
FIGS. 6A-D shows particle size and distribution of gelatin/gold nanoreactors incubated under different conditions.
Figure 6B:
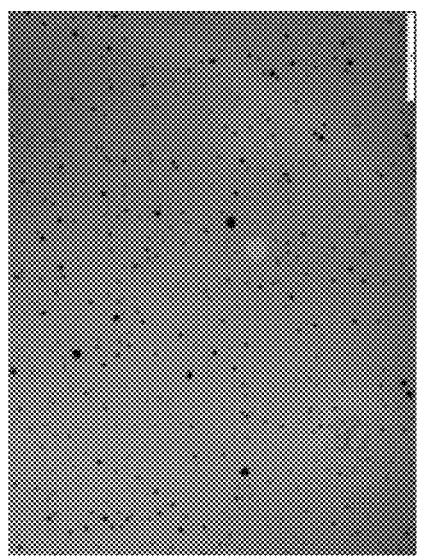
Figure 6C:
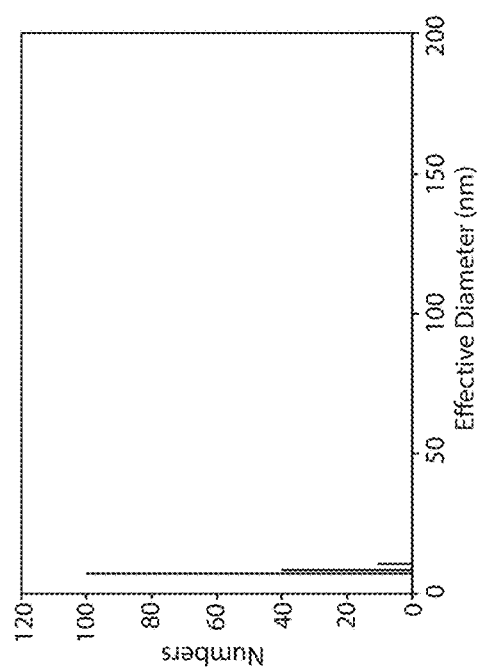
Figure 6D:
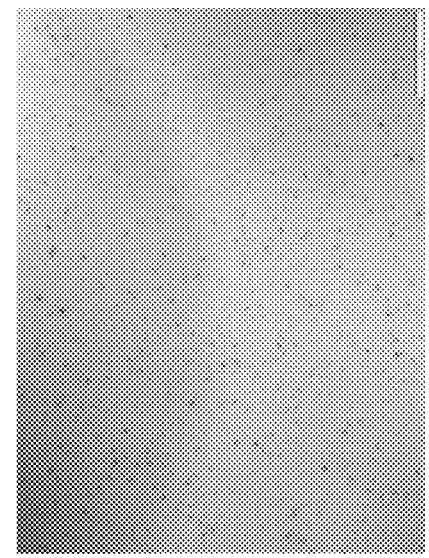

FIGS. 6A and 6B show plots of the number of nanoparticles versus effective diameter for the nanoreactors incubated at higher temperature and lower temperature, respectively. Those figures confirm that the nanoparticles produced at higher temperature are fairly uniform in size and are, on average, about 10 nm. The nanoparticles produced at lower temperature show a wider distribution in size, with the greatest number of particles clustered around 50 nm. In addition, at lower temperature, nanoparticles reached about 130 nm in size.

Though not intending to be bound to any particular theory, based on the forgoing experiments, it appears that at higher temperature, nucleation occurs at a faster rate, so that a greater number of smaller nanoparticles are formed, with less nanoparticle growth occurring. In contrast, at lower temperature, it appears that nucleation occurs more slowly, so the available precursor is used to grow the existing particles, resulting in a smaller number of larger nanoparticles. Those effects suggest that the reduction of the gold precursor by the gelatin occurs at a faster rate at higher temperature and a slower rater at lower temperature.

At either temperature, once nuclei are formed, newly-reduced precursors either participates in forming a new nucleus or joins an existing nucleus to grow particle size. Since nucleation involves local saturation of reduced precursor, and growth follows nucleation, faster reducing rates (at higher temperature) increase the chance of nucleation, and much of the precursor is used in nucleation rather than growth. Conversely, slower reducing rates (at lower temperature) mean a lower chance of local saturation to nucleate a particle, resulting in a smaller number of particles and the reduced precursor is then used to grow those particles.

The nanoparticle attributes, such as number, shape, most dominant size, size distribution, and aggregation may also be determined by the responses of the nanoreactor to its thermal history. Further, such particle attributes result in the distinguishable color of the nanoreactor. Since nanoparticle synthesis is induced by gelatin oxidation in this system, the status of nanoparticle formation should be affected by gelatin's response to thermal stress.

Example 7: Gold Nanoparticle Formation Under Varying Temperature Conditions

To determine the effect of varying temperature on the formation of gold nanoparticles, nanoreactors were prepared and incubated under the following conditions: (1) 90° C. for 14 minutes ("HTST"); (2) 90° C. for 14 minutes, followed by 60° C. for 200 minutes ("HTST-LTLT"); (3) 60° C. for 200 minutes ("LTLT"); and (4) 60° C. for 200 minutes, followed by 90° C. for 14 minutes ("LTLT-HTST"). The UV-Vis spectrum of each of the nanoreactors is shown in FIG. 7A. While the HTST and LTLT conditions resulted in similar peak absorption values (with different peak wavelengths), see "1" and "3" in FIG. 7A, the HTST-LTLT condition resulted in a dramatic increase in absorbance, see "2" in FIG. 7A, while the LTLT-HTST condition resulted in only a modest increase in absorbance, see "4" in FIG. 7A.

FIG. 7B shows the particle size distribution of the HTST (1) and the HTST-LTLT (2) conditions. FIG. 7B(2) also shows the TEM of the HTST-LTLT condition. FIG. 7C shows the particle size distribution of the LTLT (1) and the LTLT-HTST (2) conditions. FIG. 7C(2) also shows the TEM of the LTLT-HTST condition. Those results suggest that the first temperature condition determines the size distribution of the particles. That is, if the sample is subjected to high temperature first, a larger number of smaller particles are formed, even if the sample is subsequently subjected to lower temperature. The size of those particles grows slightly during lower temperature incubation, but not dramatically. Compare FIG. 7B, (1) and (2). If the sample is subjected to low temperature first, a smaller number of larger particles are formed, even if the sample is subsequently subjected to a higher temperature. The size of those particles grows significantly during the higher temperature incubation. Compare FIG. 7C, (1) and (2).

While not intending to be bound by any theory, these results suggest that, for the HTST-LTLT condition, during the initial high temperature incubation, many nuclei are formed by reduction of gold precursor during the high temperature phase. During the subsequent low temperature phase, those nuclei grow, resulting in a large number of small nanoparticles, causing a dramatic increase in absorbance. For the LTLT-HTST condition, relatively few, larger nanoparticles are formed during the low temperature phase. During the subsequent high temperature phase, the existing nanoparticles grow dramatically in size, but there is relatively little formation of new nuclei, possibly due to a depletion of available precursor.

The foregoing description is considered as illustrative only and is not intended to limit the claimed invention. Numerous modifications and changes may readily occur to those skilled in the art. The invention is not limited to the exact construction and operation shown and described, and accordingly, all suitable modifications and equivalents are considered to fall within the scope of the invention.

We claim:

1. Packaging for the detection of exposure of a perishable good to an elevated temperature, the packaging comprising:
   (a) a container configured to house one or more units of the perishable good and
   (b) a nanoreactor system,
   wherein the nanoreactor system encases a nanoreactor suitable for inclusion with the perishable good,
   wherein the nanoreactor comprises a metal precursor and a biopolymer carrier in a solvent,
   wherein the biopolymer carrier is capable of acting as a reducing agent to reduce the metal precursor to form a nanoparticle therefrom when the perishable good is exposed to the elevated temperature;
   and wherein the nanoreactor system is associated with the container.

2. The packaging of claim 1, wherein the perishable good comprises a member selected from the group consisting of a food, a pharmaceutical, a biologic, a polymeric good, a petroleum product, and a fabric.

3. The packaging of claim 1, wherein the nanoreactor system is associated within the container.

4. The packaging of claim 1, wherein the nanoreactor system is associated outside the container.

5. The packaging of claim 1, wherein the nanoreactor system is anchored to the container.

6. The packaging of claim 1, wherein the container comprises a multiplicity of smaller containers and wherein the multiplicity of smaller containers house one or more units of the perishable good.

7. The packaging of claim 6, wherein the nanoreactor system is associated with each of the multiplicity of smaller containers.

8. The packaging of claim 1, wherein the biopolymer carrier is gelatin.

9. The packaging of claim 1, wherein the biopolymer carrier is present at a concentration of between 0.01 g/mL and 0.1 g/mL.

10. The packaging of claim 1, wherein the metal precursor is gold.

11. The packaging of claim 1, wherein the metal precursor is present at a concentration of between 0.1 mM and 5 mM.

12. Packaging for the detection of exposure of a perishable good to an elevated temperature, the packaging comprising:
    (a) a container housing one or more units of a perishable good and
    (b) a nanoreactor system,
    wherein the nanoreactor system encases a nanoreactor suitable for inclusion with the perishable good,
    wherein the nanoreactor comprises a metal precursor and a carrier in a solvent, wherein the carrier is gelatin and is present at a concentration of between 0.01 g/mL and 0.1 g/mL in the nanoreactor and wherein the metal precursor is gold ions present at a concentration between 0.1 mM and 5 mM in the nanoreactor,
    wherein the carrier is capable of acting as a reducing agent to reduce the metal precursor to form a nanoparticle therefrom when the perishable good is exposed to the elevated temperature, and wherein the nanoreactor system is associated with the container.

13. A method for the detection of exposure of a perishable good to an elevated temperature, the method comprising detecting formation of nanoparticles in a nanoreactor system that is associated with a container housing the perishable good, wherein detecting formation of nanoparticles in the nanoreactor system indicates that the perishable good was exposed to the elevated temperature.

14. The method of claim 13, wherein the container is configured to house one or more units of the perishable good, and the nanoreactor system encases a nanoreactor suitable for inclusion with the perishable good, wherein the nanoreactor comprises a metal precursor and a biopolymer carrier in a solvent, and wherein the biopolymer carrier is capable of acting as a reducing agent to reduce the metal precursor to form a nanoparticle therefrom when the perishable good is exposed to the elevated temperature.

15. The method of claim 14, wherein the biopolymer carrier is gelatin.

16. The method of claim 14, wherein the biopolymer carrier is present at a concentration of between 0.01 g/mL and 0.1 g/mL.

17. The method of claim 14, wherein the metal precursor is gold.

18. The method of claim 14, wherein the metal precursor is present at a concentration of between 0.1 mM and 5 mM.

19. The method of claim 14, wherein a color of the nanoreactor is determined by visual inspection in order to detect the formation of nanoparticles in the nanoreactor system.

20. The method of claim 13, wherein the perishable good comprises a member selected from the group consisting of a food, a pharmaceutical, a biologic, a polymeric good, a petroleum product, and a fabric.

21. The method of claim 13, wherein detecting formation of nanoparticles comprises detecting a characteristic selected from color, peak wavelength, peak shape, absorbance, nanoparticle size, nanoparticle size distribution, and nanoparticle number.

* * * * *